(12) United States Patent
Chen et al.

(10) Patent No.: US 9,168,503 B2
(45) Date of Patent: Oct. 27, 2015

(54) REACTION SYSTEM AND PROCESS FOR PREPARING POLYMETHOXY DIMETHYL ETHER

(71) Applicants: Suzhou OST Advanced Materials Co., Ltd., Suzhou, Jiangsu (CN); Lanzhou Institute of Chemical Physics, Chinese Academy of Sciences, Lanzhou, Gansu (CN)

(72) Inventors: Jing Chen, Lanzhou (CN); Heyuan Song, Lanzhou (CN); Chungu Xia, Lanzhou (CN); Meirong Kang, Lanzhou (CN)

(73) Assignees: Suzhou OST Advanced Materials Co., Ltd., Suzhou (CN); Lanzhou Institute of Chemical Physics, Chinese Academy Of Sciences, Lanzhou (CN)

( * ) Notice: Subject to any disclaimer, the term of this patent is extended or adjusted under 35 U.S.C. 154(b) by 0 days.

(21) Appl. No.: 14/218,552

(22) Filed: Mar. 18, 2014

(65) Prior Publication Data
US 2015/0094497 A1    Apr. 2, 2015

(30) Foreign Application Priority Data
Sep. 29, 2013    (CN) .......................... 2013 1 0455313

(51) Int. Cl.
*B01J 14/00*    (2006.01)
*C07C 41/01*    (2006.01)
*C07C 41/56*    (2006.01)
*C07C 41/58*    (2006.01)
*B01D 3/00*    (2006.01)

(52) U.S. Cl.
CPC ................. *B01J 14/00* (2013.01); *B01D 3/009* (2013.01); *C07C 41/01* (2013.01); *C07C 41/56* (2013.01); *C07C 41/58* (2013.01); *B01J 2219/00006* (2013.01)

(58) Field of Classification Search
CPC ......... B01J 14/00; B01J 14/005; C07C 41/56; C07C 41/50
See application file for complete search history.

(56) References Cited

U.S. PATENT DOCUMENTS 6,534,685 B1    3/2003    Patrini et al.
7,235,113 B2    6/2007    Sanfilippo et al.
(Continued)

FOREIGN PATENT DOCUMENTS

CA    2 581 502 A1    5/2006
EP    1 505 049 A1    2/2005
WO    2006/045506 A1    5/2006

*Primary Examiner* — Lessanework Seifu
(74) *Attorney, Agent, or Firm* — Seed IP Law Group PLLC (57) ABSTRACT

The invention relates to a reaction system and process for continuously preparing polymethoxy dimethyl ether ($DMM_{3-8}$) by a continuous acetalization reaction between an aqueous formaldehyde solution or paraformaldehyde and methanol in the presence of a functionalized acidic ionic liquid as a catalyst. The reaction system of the invention preferably comprises a formaldehyde-concentrating unit, a vacuum-drying unit, an acetalization reaction unit, a product-separating unit and a catalyst-regenerating unit. The process of the invention uses aqueous formaldehyde solution as an initial raw material, which is concentrated in the formaldehyde-concentrating unit to a concentrated formaldehyde of 50~80 wt. %, and vacuum-dried to paraformaldehyde, or uses paraformaldehyde as raw material directly, then obtains $DMM_{3-8}$ by an acetalization reaction. The raw materials of the reaction used in the invention are cheap and available easily, and the utilization rate of formaldehyde is high; an efficient separation between the catalyst and product, as well as the reuse of the catalyst and raw materials, are realized by a separation mode of combining extraction and rectification together.

13 Claims, 2 Drawing Sheets

(56) References Cited

U.S. PATENT DOCUMENTS

| | | |
|---|---|---|
| 2007/0260094 A1 | 11/2007 | Schelling et al. |
| 2008/0207954 A1 | 8/2008 | Stroefer et al. |
| 2011/0288343 A1 | 11/2011 | Chen et al. |
| 2011/0313202 A1 | 12/2011 | Xia et al. |
| 2014/0114092 A1* | 4/2014 | Xia et al. .................. 568/601 |
| 2014/0114093 A1* | 4/2014 | Chen et al. ................. 568/613 |

* cited by examiner

REACTION SYSTEM AND PROCESS FOR PREPARING POLYMETHOXY DIMETHYL ETHER

TECHNICAL FILED

The present invention relates to a novel reaction system and process for continuously preparing polymethoxy dimethyl ether, more particularly, to a novel reaction system and process for continuously preparing polymethoxy dimethyl ether by a continuous acetalization reaction between an aqueous formaldehyde solution or paraformaldehyde and methanol in the presence of a functionalized acidic ionic liquid as a catalyst.

BACKGROUND ART

The middle part of polymethoxy dimethyl ether ($CH_3O(CH_2O)_nCH_3$, $DMM_n$, n=1–8) is paraformaldehyde, and the both ends thereof are terminated by methyl groups. $DMM_n$, wherein n is ≤5, has excellent solubility and very high permeability, is miscible with water and many organic solvents, and can be widely used in industrial solvents, pigment dispersants, or the like. $DMM_n$ is also an oxygen-containing blending component with great potential for diesel fuel, which has high cetane numbers ($DMM_2$: 63, $DMM_3$: 78, $DMM_4$: 90, $DMM_5$: 100) and high oxygen contents (42%-49%). Addition of $DMM_n$ in a amount of 10-20 v/v % to diesel fuel can improve the combustion characteristics of the diesel fuel significantly, increase the thermal efficiency effectively, and reduce the emission of $NO_x$ and carbon soot greatly. It was reported (U.S. Pat. No. 7,235,113) that the emission of the $NO_x$, particulates and hydrocarbons in the exhaust gas can satisfy the Euro V criteria by adding 15 v/v % of $DMM_{3-6}$ to diesel fuel.

A conventional process for synthesizing $DMM_n$ is by the acetalization reaction between a compound providing paraformaldehyde and a compound providing methyl groups for termination in the presence of an acidic catalyst. Since 2001, Snamprogetti S. P. A. (EP 1505049 A1, U.S. Pat. No. 6,534,685), BASF (WO 2006/045506 A1, CA 2581502 A1, US 20070260094 A1) and the like successively developed the processes for continuously preparing $DMM_n$ by the reaction between paraform or trioxymethylene and methanol, in which a liquid acid such as $H_2SO_4$ or $CF_3SO_3H$ is employed as the catalyst; after the completion of the reaction, the catalyst and the by-product water were removed from the reaction liquid by adsorption with a silica gel or resin; then a two-stage rectification process is used to separate the unreacted raw materials, light components ($DMM_{1-2}$), products ($DMM_{3-5}$) and heavy components ($DMM_{n \geq 5}$); and the raw materials of the reaction, the light components and the heavy components are recycled to the reactor for reuse. In the above-mentioned separation process, a great amount of adsorbents are used, the energy consumption is large, the catalyst cannot be recycled, and the cost of the raw materials is relatively high.

In 2008, BASF AG (US 20080207954 A1) investigated a process for preparing $DMM_{1-5}$ by the reaction between formaldehyde and methanol in an aqueous solution, in which a liquid acid or a solid acid is used as a catalyst; the reaction liquids ($DMM_{1-5}$, unreacted raw materials and water) are distilled out from the top of the rectification tower by the reaction rectification technique; then the light components ($DMM_{1-2}$ and unreacted raw materials), the crude product ($DMM_{3-4}$ and water) and the heavy components ($DMM_{n>4}$) are separated by a multi-stage rectification process. $DMM_{3-4}$ and water are separated by a phase separation technique from the crude product, and the light components and the heavy components are recycled to the reaction unit for reuse. During the practical operation, however, methanol, water and $DMM_n$ tend to form an azeotrope, so it is difficult to separate methanol from $DMM_{3-4}$, and methanol has good miscibility with water together with $DMM_{3-4}$, which renders the phase separation to be difficult.

In recent years, Lanzhou Institute of Chemical Physics, Chinese Academy of Sciences reported (U.S. Pat. Nos. 1,315, 439, 13/164,677) a process for synthesizing $DMM_n$ by catalyzing the reaction between trioxymethylene and methanol with an ionic liquid, in which the reaction liquids were sequentially subjected to the following processes: flash distillation, thin film evaporation separation and phase separation, and thus the separation of the light components ($DMM_{1-2}$, a portion of water, unreacted raw materials), the crude product $DMM_{3-8}$, and the catalyst, are achieved. However, the crude product still contains a small amount of water and the catalyst, which need to be removed by adsorption with silica gel or an anion exchange resin in order to realize the refining of the product $DMM_{3-8}$. In this process, the recovery rate of the catalyst is relatively low, the cost of the raw materials of the reaction is high, and the process flow is long.

SUMMARY OF THE INVENTION

An object of the invention is to provide a system and process for preparing polymethoxy dimethyl ether $DMM_{3-8}$ by a continuous acetalization reaction between an aqueous formaldehyde solution or paraformaldehyde and methanol in the presence of a functionalized acidic ionic liquid as a catalyst.

Thus, in one aspect, there provided a reaction system for continuously preparing polymethoxy dimethyl ether with an aqueous formaldehyde solution or paraformaldehyde as raw material, which comprises:

1) an optional formaldehyde-concentrating unit, which is used to concentrate an aqueous formaldehyde solution of 37~40 wt. % to obtain a concentrated formaldehyde of 50~80 wt. %;

2) an optional vacuum-drying unit, which is used to polymerize the concentrated formaldehyde obtained from the formaldehyde-concentrating unit to paraformaldehyde (preferably, the polymerization degree is 8~16);

3) an acetalization reaction unit, which is used to subject the concentrated formaldehyde obtained from the formaldehyde-concentrating unit, the paraformaldehyde obtained from the vacuum-drying unit or paraformaldehyde added directly from the exterior to an acetalization reaction with methanol in the presence of an acidic ionic liquid as a catalyst, so as to obtain a crude product, $DMM_{1-8}$; and 4) a product-separating unit, which is used to separate the desired product, $DMM_{3-8}$ from the crude product obtained from the acetalization reaction unit.

In a preferred embodiment, the formaldehyde-concentrating unit comprises a formaldehyde heater, a formaldehyde concentrator, a dilute-aldehyde condenser, a column washer and a washing liquor tank, wherein the aqueous formaldehyde solution is evaporated in the formaldehyde heater to give a vapor-liquid mixed fluid; the vapor-liquid mixed fluid is fed into the formaldehyde concentrator to give a (liquid) concentrated formaldehyde of 50~80 wt. %; and the gas generated during this process is fed into the dilute-aldehyde condenser to recover formaldehyde, and the non-condensable gases coming out from the dilute-aldehyde condenser are fed into the column washer to be absorbed by the washing liquor and fed into the washing liquor tank.

In a preferred embodiment, the vacuum-drying unit is a continuous vacuum dryer, and under conditions of 60~80° C. and a gauge pressure of −0.1~−0.05 MPa, the liquid concentrated formaldehyde obtained from step 1) is polymerized to a paraformaldehyde having a polymerization degree of 8~16.

In a preferred embodiment, the acetalization unit comprises a single-stage or multi-stage reactor and a vapor condenser.

In a preferred embodiment, the single-stage or multi-stage reactor is a single-stage or multi-stage shell and tube reactor or an overflow kettle.

In a preferred embodiment, the reaction system further comprises a catalyst-regenerating unit, which comprises a thin film evaporator, and is used to receive the heavy phase separated from the product-separating unit and recycle the catalyst in the heavy phase back to the acetalization reaction unit after the catalyst is dehydrated.

In a preferred embodiment, the product-separating unit comprises an extraction tower and a single-stage or multi-stage rectification tower, and the extraction tower and the single-stage or multi-stage rectification tower are connected with each other in series; and the extraction tower separates the crude product $DMM_{1-8}$ into a light phase and a heavy phase, wherein the heavy phase comprises the acidic ionic liquid catalyst, formaldehyde and water, and the light phase comprises unreacted methanol and formaldehyde, $DMM_{1-8}$ as well as an extraction agent. Preferably, the light phase is continuously flowed into a rectification unit from the top of the extraction tower, so that the recycled material (formaldehyde, methanol and $DMM_{1-2}$), the extraction agent and the desired product $DMM_{3-8}$ are separated; the recycled material is fed back to the acetalization reactor; the extraction agent is fed back to the extraction tower for reuse; the heavy phase is flowed into the catalyst-regenerating unit from the tower bottom.

In a preferred embodiment, the rectification tower comprises a light component rectification tower, an extraction agent rectification tower and a product rectification tower.

In a preferred embodiment, the rectification tower is a tray tower or a packed tower, and the number of tower tray is 3~10.

In another aspect, there provided a process for continuously preparing polymethoxy dimethyl ether with an aqueous formaldehyde solution or paraformaldehyde as raw material, which comprises the following steps:

1) optionally, in a formaldehyde concentrator, under conditions of 50~90° C. and a gauge pressure of −0.1~−0.05 MPa, concentrating an aqueous formaldehyde solution of 37~40 wt. % to obtain a concentrated formaldehyde having a concentration of 50~80 wt. %; further feeding the gas generated during this process into a dilute-aldehyde condenser, washing and recovering formaldehyde;

2) optionally, feeding the concentrated formaldehyde obtained from step 1) into a vacuum drier, and under conditions of 60~80° C. and a gauge pressure of −0.1~−0.05 MPa, and obtaining paraformaldehyde (preferably, the polymerization degree is 8~16) by polymerization;

3) in an acetalization reactor, subjecting the concentrated formaldehyde from step 1), the paraformaldehyde from step 2) or paraformaldehyde added directly from the exterior to a continuous acetalization reaction with methanol by using functionalized acidic ionic liquid as a catalyst, so as to form a reaction effluent liquid, which comprises polymethoxy dimethyl ether $DMM_{1-8}$, water, unreacted raw materials and the catalyst; and 4) in an extraction tower, extracting the reaction effluent liquid obtained from step 3) with an extraction agent to give a light phase and a heavy phase, wherein the light phase comprises the extraction agent, $DMM_{1-8}$, parts of methanol and formaldehyde, while the heavy phase comprises the catalyst and an aqueous formaldehyde solution; separating the recycled material comprising formaldehyde, methanol and $DMM_{1-2}$, the extraction agent and the desired product $DMM_{3-8}$ by rectifying the light phase; feeding the recycled material back to an acetalization reactor; feeding the extraction agent back to an extraction tower for reuse; continuously flowing the heavy phase into a catalyst-regenerating unit from the tower bottom.

In a preferred embodiment, the process further comprises: in the catalyst-regenerating unit, evaporating the aqueous solution of the catalyst from step 4) so as to separating most of water, and feeding the recovered catalyst back to step 3) for reuse.

In a preferred embodiment, in step 3), the molar ratio of the concentrated formaldehyde or the paraformaldehyde to methanol is 0.5~3.0.

In a preferred embodiment, in step 3), the reaction temperature is 100~130° C., the reaction pressure is 2.0~5.0 MPa, and the reaction resident time is 60~180 min.

In a preferred embodiment, the extraction agent in step 4) is one or more selected from n-hexane, cyclohexane, petroleum ether, chloroform, benzene, toluene, xylene, and ethyl acetate.

In a preferred embodiment, the extraction agent in step 4) is cyclohexane, benzene or toluene.

In a preferred embodiment, the cation moiety of the functionalized acidic ionic liquid catalyst is one selected from an acid-functionalized quaternary amine cation, an acid-functionalized quaternary phosphine cation, an acid-functionalized imidazole cation or an acid-functionalized pyridine cation, and the anion moiety thereof is one selected from p-toluenesulfonate anion, trifluoromethanesulfonate anion, methylsulfonate anion, bisulfate anion, or trifluoroacetate anion.

The invention includes, but is not limited to, the following advantages:

1. The invention prepares polymethoxy dimethyl ether by using the aqueous formaldehyde solution or paraformaldehyde as raw material, thus such raw materials are cheap and available easily.

2. The invention prepares polymethoxy dimethyl ether by continuous concentration and acetalization reaction process of formaldehyde, thus the process is simple and the process flow is short, which extremely saves the equipment costs and the energy consumption.

3. The corrosivity of the catalyst is low, so the 316L stainless steel can be used as the material of the reactor, thus the cost of the device is low. Furthermore, the acetalization reaction realizes the reuse of the catalyst, which further reduces the cost.

4. The separation of the by-product water of the acetalization reaction unit from the $DMM_n$ as well as the raw materials is realized, which destroys the azeotropy of water and $DMM_n$, methanol, formaldehyde, and thus the separation of the desired product $DMM_{3-8}$ and the recycle of materials are realized effectively.

BRIEF DESCRIPTION OF DRAWINGS

It should be appreciated that these drawings are only schematic flow charts for illustrating the technical solutions of the invention, wherein only the equipments necessary for illustrating the process are shown. For conciseness and clarity, other necessary devices, such as meters, gas confluence devices, valves, intermediate tanks and the like, are omitted.

DETAILED DESCRIPTION OF EMBODIMENTS

The invention can prepare polymethoxy dimethyl ether $DMM_{3-8}$ with an aqueous formaldehyde solution of 37~40 wt. % as the starting material via continuous concentration, vacuum drying and acetalization reaction, or the invention prepares polymethoxy dimethyl ether $DMM_{3-8}$ by using paraformaldehyde as the starting material directly via acetalization reaction.

In one specific embodiment, a reaction system of the invention for preparing $DMM_{3-8}$ with an aqueous formaldehyde solution as the raw material (hereinafter, referred to as "the reaction system of the invention") comprises:

1) a formaldehyde-concentrating unit, which is used to concentrate an aqueous dilute formaldehyde solution to a liquid concentrated formaldehyde having a concentration of 50~80 wt. %. Preferably, the formaldehyde-concentrating unit comprises a formaldehyde concentrator, a formaldehyde heater, a dilute-aldehyde condenser, a column washer and a washing liquor tank, wherein the aqueous formaldehyde solution of 37~40 wt. % is evaporated in the formaldehyde heater to give a vapor-liquid mixed fluid; the vapor-liquid mixed fluid is fed into the formaldehyde concentrator, and preferably concentrated under the conditions of 50~90° C. and −0.1~−0.05 MPa (gauge pressure), so that a liquid concentrated formaldehyde having a concentration of 50~80 wt. % is obtained; the gas generated during this process is fed into a dilute-aldehyde condenser, so as to wash and recover formaldehyde;

2) a vacuum-drying unit, which is used to polymerize the concentrated formaldehyde obtained from the formaldehyde-concentrating unit 1) to give paraformaldehyde. Preferably, the vacuum-drying unit is a continuous vacuum drier. Preferably, a paraformaldehyde having the polymerization degree of 8~16 is obtained under the conditions of 60~80° C. and −0.1~−0.05 MPa (gauge pressure);

3) an acetalization reaction unit, which is used to subject the concentrated formaldehyde obtained in the formaldehyde-concentrating unit or the paraformaldehyde obtained from the vacuum-drying unit to an acetalization reaction with methanol in the presence of an acidic ionic liquid catalyst, so as to give a crude product $DMM_{1-8}$. Preferably, this acetalization reaction unit comprises a single-stage or multi-stage reactor or a vapor condenser; and 4) a product-separating unit, which is used to separate the desired product from the crude polymethoxy dimethyl ether obtained in the acetalization reaction unit. Preferably, this product-separating unit comprises an extraction tower and a single-stage or multi-stage rectification tower, the extraction tower and the single-stage or multi-stage rectification tower are connected with each other in series; wherein in the extraction tower, the crude $DMM_{1-8}$ is separated into a light phase and a heavy phase, and wherein the heavy phase comprises the functionalized acidic ionic liquid catalyst, formaldehyde and water, the light phase comprises unreacted methanol and formaldehyde, $DMM_1$, $DMM_2$, $DMM_{3-8}$, extraction agent. The light phase is continuously flowed into a rectification unit from the top of the extraction tower, so that the recycled material (formaldehyde, methanol and $DMM_{1-2}$), the extraction agent and the desired product $DMM_{3-8}$ are separated; the recycled material is fed back to the acetalization reactor; the extraction agent is fed back to the extraction tower for reuse; the heavy phase is flowed into the catalyst-regenerating unit from the tower bottom.

It is necessary to indicate that, in the reaction system of the invention, the formaldehyde-concentrating unit and the vacuum-drying unit are necessary only when the raw material used is an aqueous dilute formaldehyde solution, whereas they are not necessary when a liquid concentrated formaldehyde (e.g. having a concentration of 50~80 wt. %) or paraformaldehyde from the exterior (for example, purchased) is directly used as the raw material.

Preferably, the reaction system further comprises:

5) a catalyst-regenerating unit, which comprises a thin film evaporator; wherein the catalyst-regenerating unit receives the separated heavy phase from the product-separating unit, and the catalyst in the heavy phase is recycled back to the acetalization reaction unit after the catalyst is dehydrated.

In one embodiment of the reaction system of the invention, the acetalization reactor is a single-stage or multi-stage shell and tube reactor or an overflow kettle.

In one preferred embodiment of the reaction system of the invention, the 316L stainless steel can be selected as the material of the acetalization reactor.

In one embodiment of the reaction system of the invention, the rectification tower of the product-separating unit is a tray tower or a packed tower, and the number of tower tray is 3~10.

In one embodiment of the reaction system of the invention, the thin film evaporator in the catalyst-regenerating unit is selected from a falling film evaporator, a scraper type or a non-scraper type thin film evaporator.

In one preferred embodiment of the reaction system of the invention, the formaldehyde-concentrating unit comprises a formaldehyde concentrator, a formaldehyde heater, a dilute-aldehyde condenser, a column washer and a washing liquor tank; the formaldehyde concentrator is provided with an inlet, a liquid outlet and a gas outlet, wherein the liquid outlet is provided at the bottom of the formaldehyde concentrator and the gas outlet is provided at the upper portion of the formaldehyde concentrator. In this case, a feasible configuration mode is that: the outlet of the formaldehyde heater and the inlet of the formaldehyde concentrator are communicated with each other via a pipe; the liquid outlet of the formaldehyde concentrator and the inlet of the vacuum drier or the formaldehyde inlet of the acetalization reactor are communicated with each other via a pipe; the gas outlet of the formaldehyde concentrator and the inlet of the dilute-aldehyde condenser are communicated with each other via a pipe; the gas outlet of the dilute-aldehyde condenser and the gas inlet of the column washer are communicated with each other via a pipe; the liquid outlet of the column washer and the inlet of the washing liquor tank are communicated with each other via a pipe; the outlet of the washing liquor tank and the washing liquor inlet of the column washer are communicated with each other via a pipe.

In one preferred embodiment of the reaction system of the invention, in the acetalization unit, the outlet of the single-stage or multi-stage reactor and the inlet of the vapor condenser within the acetalization unit are communicated with each other via a pipe.

In one preferred embodiment of the reaction system of the invention, the rectification tower comprises a light component rectification tower, an extraction agent rectification tower and a product rectification tower. In this case, an feasible configuration mode is that: the reaction liquid inlet of the extraction tower and the outlet of the vapor condenser of the acetalization unit are communicated with each other via a pipeline; the light phase outlet of the extraction tower and the inlet of the light component rectification tower are communicated with each other via a pipeline; the heavy phase outlet of the extraction tower and the inlet of the thin film evaporator are communicated with each other via a pipeline; the liquid phase outlet of light component rectification tower and the inlet of the extraction agent rectification tower are communicated with each other via a pipeline; the liquid phase outlet of the extraction agent rectification tower and the inlet of the product rectification tower are communicated with each other via a pipeline; the gas phase outlets of the light component rectification tower and the product rectification tower and the inlet of the acetalization reactor are communicated with each other via a pipeline; the gas outlet of the extraction agent rectification tower and the inlet of the extraction agent storage tank are communicated with each other via a pipeline.

In one embodiment of the reaction system of the invention, the configuration mode of the thin film evaporator is that the heavy phase outlet and the inlet of the catalyst storage tank are communicated with each other via a pipeline.

In another specific embodiment, a process of the invention for preparing polymethoxy dimethyl ether with an aqueous formaldehyde solution or paraformaldehyde as the raw material (hereinafter, referred to as "the process of the invention") comprises the following steps:

1) in a formaldehyde concentrator, using an aqueous formaldehyde solution of 37~40 wt. % as raw material, preferably under the conditions of 50~90° C. and −0.1~−0.05 MPa (gauge pressure), obtaining a liquid formaldehyde having a concentration of 50~80 wt. %; feeding the gas generated during this process into a dilute-aldehyde condenser, washing and recovering formaldehyde;

2) feeding the liquid formaldehyde obtained from step 1) into a vacuum drier, preferably under the conditions of 60~80° C. and −0.1~−0.05 MPa (gauge pressure), to obtain paraformaldehyde, which for example has a polymerization degree of 8~16;

3) subjecting the concentrated formaldehyde from step 1) or the paraformaldehyde from step 2) to a continuous acetalization reaction with methanol by using functionalized acidic ionic liquid as a catalyst, so as to form a reaction effluent liquid which comprises resultant crude product $DMM_{1-8}$, water, unreacted raw materials and the catalyst; and 4) extracting the reaction effluent liquid obtained from step 3) with an extraction agent to give a light phase and a heavy phase, wherein the light phase comprises the extraction agent, $DMM_{1-8}$, unreacted parts of formaldehyde and methanol, and the heavy phase is the catalyst and an aqueous formaldehyde solution; the light phase is continuously flowed into a rectification unit from the tower top, so that the recycled material (formaldehyde, methanol and $DMM_{1-2}$), the extraction agent and the product $DMM_{3-8}$ are separated; the recycled material is fed back to the acetalization reactor; the extraction agent is fed back to the extraction tower for reuse; the heavy phase is flowed into the catalyst-regenerating unit from the tower bottom.

Preferably, the process of the invention further comprises: 5) evaporating the aqueous solution of the catalyst from step 4) so as to separate most of the water, and feeding the recovered catalyst back to step 3) for reuse.

In the process of the invention, the cation moiety of the functionalized acidic ionic liquid is one selected form an acid-functionalized quaternary amine cation, an acid-functionalized quaternary phosphine cation, an acid-functionalized imidazole cation or an acid-functionalized pyridine cation, and the anion moiety thereof can be one independently selected from p-toluenesulfonate anion, trifluoromethanesulfonate anion, methylsulfonate anion, bisulfate anion, or trifluoroacetate anion.

In one embodiment of the process of the invention, in step 3), the molar ratio of formaldehyde to methanol is 0.5~3.0.

In another preferred embodiment of the process of the invention, the reaction is carried out under nitrogen gas protection.

In one embodiment of the process of the invention, in step 3), the reaction temperature is 100~130° C., the reaction pressure is 2.0~5.0 MPa, and the reaction resident time is 60~180 min.

In another preferred embodiment of the process of the invention, in step 3), the catalyst accounts for 1~6 wt. % of the total reaction raw materials.

In one embodiment of the process of the invention, the extraction agent in step 4) is one or more selected from n-hexane, cyclohexane, petroleum ether, chloroform, benzene, toluene, xylene, and ethyl acetate, preferably, cyclohexane, benzene or toluene.

In another preferred embodiment of the process of the invention, in step 4), the used amount of the extraction agent is 1~3 folds more than the reaction liquid in terms of volume.

In one embodiment of the process of the invention, the temperature for the extraction in step 4) is 20~40° C.

In one embodiment of the process of the invention, in step 5), the evaporation temperature is 60~70° C., and the gauge pressure is −0.1~−0.05 MPa.

It should be indicated here that the above-mentioned process parameters and reaction materials, such as the raw materials, extraction agent, catalyst and the like, which are used in the process of the invention, also can be used in the reaction system of the invention.

The process flow and process equipments will be described in detail with reference to the drawings (the A, B, C, D and E zones mentioned below correspond to the zones indicated by the reference signs A, B, C, D and E in FIG. 1, respectively):

A. In the formaldehyde-concentrating zone A (corresponding to the "formaldehyde-concentrating unit" in the reaction system of the invention), an aqueous formaldehyde solution (for example, 37~40 wt. %) is evaporated in the formaldehyde heater, so as to obtain a vapor-liquid mixed fluid. The vapor-liquid mixed fluid is fed into the formaldehyde concentrator. Under the conditions of 50~90° C. and −0.1~−0.05 MPa (gauge pressure), a liquid formaldehyde having a high concentration and a vapor formaldehyde having a low concentration are separated quickly, and a formaldehyde solution of 50-80 wt. % is obtained and fed to the vacuum drier in B zone via a concentrated-aldehyde pump, or to the acetalization reactor in C zone directly. The vapor phase is fed into the dilute-aldehyde condenser, where it is condensed to form a liquid dilute formaldehyde, which is fed into the dilute-aldehyde receiving tank. The non-condensable gas withdrawn out from the dilute-aldehyde condenser is fed into the column washer to be absorbed by washing liquor (desalinized water), and the gas is drawn by a vacuum pump and emitted to the atmosphere.

B. In the vacuum drying zone B (corresponding to the "vacuum-drying unit" in the reaction system of the invention), the aqueous formaldehyde solution of 50~80 wt. % from A zone is vacuum dried (for example, under the conditions of 60~80° C. and −0.1~−0.05 MPa (gauge pressure)) by using a continuous vacuum dryer, so as to obtain paraformaldehyde having a polymerization degree of 8~16.

C. In the acetalization reaction zone C (corresponding to the "acetalization reaction unit" in the reaction system of the invention), in a single-stage or multi-stage reactor, the aque- ous formaldehyde solution of 50~80 wt. % from A zone or the paraformaldehyde from B zone is subjected to a continuous acetalization reaction with methanol by using a functionalized acidic ionic liquid as a catalyst (for example, under the conditions of 100~130° C. and 2.0~5.0 MPa (gauge pressure)). The reactor effluent liquid flowing out continuously comprises the above-mentioned unreacted raw materials and the catalyst in addition to the $DMM_{1-8}$ formed.

D. In the product-separating zone D (corresponding to the "product-separating unit" in the reaction system of the invention), the reactor effluent liquid flowing out from the abovementioned C zone is decompressed and continuously flowed into the extraction tower. $DMM_{1-8}$ and raw materials of the reaction are extracted by using an extraction agent. The light phase is the product phase, and is flowed into the rectification unit from the tower top continuously. The recycled material, extraction agent and the desired product $DMM_{3-8}$ are separated. The heavy phase is the catalyst and an aqueous formaldehyde solution, and is flowed into the catalyst-regenerating zone.

E. In the catalyst-regenerating zone E (corresponding to the "catalyst-regenerating unit" in the reaction system of the invention), the catalyst and the aqueous formaldehyde solution from D zone are fed into the thin film evaporator continuously. Most of the water is separated. The recovered catalyst is continuously flowed into C zone for reuse.

The process flow of the invention is described in detail below.

The reaction formulae employed in the process of the invention are as follows:

In the reaction formulae, n is an integer from 1 to 8, m is an integer from 8 to 16, IL represents a functionalized acidic ionic liquid catalyst.

The functionalized acidic ionic liquid catalyst can be selected with reference to the preferred examples below.

The structural formula of an example of the acid-functionalized quaternary amine cation of the functionalized acidic ionic liquid catalyst used in the invention can be:

wherein n is an integer of 1~6; R, $R_1$, and $R_2$ are linear alkanes having a carbon number of 1~16, or a benzene ring;
X is —$SO_3H$, —COOH or —$SO_3CH_3$.

The structural formula of an example of the acid-functionalized quaternary phosphine cation of the functionalized acidic ionic liquid catalyst used in the invention can be:

wherein n is an integer of 1~6; R, $R_1$, and $R_2$ are linear alkanes having a carbon number of 1~16, or a benzene ring;
X is —$SO_3H$, —COOH or —$SO_3CH_3$.

The structural formula of an example of the acid-functionalized imidazole cation of the functionalized acidic ionic liquid catalyst used in the invention can be:

wherein n is an integer of 1~6; R is alkyl having a carbon number of 1~16, or aryl, or H;
X is —$SO_3H$, —COOH or —$SO_3CH_3$.

The structural formula of an example of the acid-functionalized pyridine cation of the functionalized acidic ionic liquid catalyst used in the invention can be:

wherein n is an integer of 1~6; R is alkyl having a carbon number of 1~16, or aryl, or H;
X is —$SO_3H$, —COOH or —$SO_3CH_3$.

Examples of anions of the acidic ionic liquid catalyst used in the invention include:
$CH_3(C_6H_4)SO_3^-$, $CF_3SO_3^-$, $CH_3SO_3^-$, $HSO_4^-$, $CF_3COO^-$ etc.

It should be indicated here that all of the pressures used herein are in terms of gauge pressure, unless otherwise indicated. Additionally, in the following description of the process and method, some equipments, which are not shown in the drawings, may be referred. As mentioned above, these equipments are omitted only for the purpose that the main equipments of the invention can be described and showed concisely and conveniently, which does not mean that these equipments are absent or unnecessary.

Furthermore, it should be understood that the description and examples below are only preferred embodiments for illustrating the invention, and are not intended to limit the scope of the invention. Therefore, the equipments used in the reaction system of the invention are not merely limited to the specific equipments mentioned below. Based on the teaching of the invention, those skilled in the art can choose appropriate equipments having similar functions according to the specific situations.

The process flow of the invention will be described with reference to the specific configuration of the processing equipments shown in FIG. 1 and the diagram of the flow direction of the materials shown in FIG. 2.

(1) When the reaction is started or the catalyst is supplemented, the catalyst is transported to the reactor R1 (corresponding to the single-stage or multi-stage reactor of the reaction system of the invention) through the pipeline 14 via the pump from the fresh catalyst storage tank V6;

(2) Concentrating Formaldehyde

The aqueous formaldehyde solution having a concentration of 37~40 wt. % in the formaldehyde storage tank V2 is fed into the formaldehyde heater E1 via the formaldehyde pump P1. Evaporation is carried out to give the vapor-liquid mixed fluid. The vapor-liquid mixed fluid is fed into the formaldehyde concentrator S1 through the pipeline 2. Under the conditions of 50~90° C. and −0.1~−0.05 MPa, the liquid formaldehyde having a high concentration and the vapor formaldehyde having a low concentration are separated quickly. The vapor phase is fed into the dilute-aldehyde condenser E2 through the pipeline 3, and condensed to form a liquid dilute formaldehyde, which is fed into the dilute-aldehyde receiving tank V3 through pipeline 7. The non-condensable gas withdrawn from E2 is fed into the column washer C1 through the pipeline 6, and absorbed by the washing liquor (desalinized water). The gas is drawn through the pipeline 10 via the vacuum pump P3 and emitted to atmosphere. The liquid is fed into the washing liquor tank V4 through the pipeline 8, and then, together with the washing liquor, fed into the column washer again for reuse through the washing liquor-recycling pump P2 and the pipeline 9. The resultant liquid phase is formaldehyde solution of 50~80 wt. %, which is transported to the vacuum drier E3 in B zone through the pipeline 4, or to the acetalization reactor R1 in C zone directly through the pipeline 5.

(3) Vacuum Drying Formaldehyde

The aqueous formaldehyde solution of 50~80 wt. % is fed into the vacuum drier E3 through the pipeline 4, and vacuum dried under the conditions of 60~80° C. and −0.1~−0.05 MPa, so as to give paraformaldehyde having a polymerization degree of 8~16. The water is drawn via the vacuum pump P4 through the pipeline 11 and emitted to atmosphere. The paraformaldehyde may be continuously fed into the acetalization reactor R1 through the pipeline 12.

(4) Acetalization Reaction

The whole system is replaced with $N_2$, and the oxygen content measured by the measuring system for the emitted exhaust gas is lower than 10 ppm. The raw material of the concentrated formaldehyde through the pipeline 5 or paraformaldehyde through the pipeline 12, methanol (methanol storage tank V5) through the pipeline 13, recycled stocks through the pipeline 16, recycled catalyst through the pipeline 15, are respectively fed into the acetalization reactor R1 continuously in a dosing mode. $N_2$ is purified by a purification unit, and fed into the reactor R1 through the pipeline 19 in a dosing mode. The acetalization reaction is occurred at a certain temperature and a certain pressure. The reaction liquid flowing out from the bottom of the reactor R1 is fed into the heat exchanger E4 through the pipeline 17 via the pump P5, and fed back to the reactor R1 through the pipeline 18 again. The reactor and the heat exchanger are communicated with each other circularly. The reaction liquid is circulated in the reactor and the heat exchanger. The reaction liquid discharged from the top of the reactor R1 comprises the catalyst, $DMM_{1-8}$, water, unreacted methanol and formaldehyde.

(5) Separating $DMM_n$ by Extraction

The effluent liquid of the reactor R1 is transported to the heat exchanger E5 through the pipeline 20, cooled in the decompressor V9, and fed into the extraction tower C2 through the pipeline 21 after decompression. The extraction agent is delivered from the storage tank V1 into the extraction tower C2 through the pipeline 22. The reaction liquid is counter-contacted with the extraction agent sufficiently. The light phase (the product phase) is continuously fed from the tower top into the rectification tower C3 through the pipeline 23. The heavy phase (the catalyst, aqueous formaldehyde solution) is continuously fed from the tower bottom into the film evaporator S2 through the pipeline 24

(6) Separating $DMM_n$ by Rectification

The composition of the product phase is $DMM_{1-8}$, the extraction agent, unreacted methanol and formaldehyde. The product phase is rectified in the rectification tower C3. The light component (mainly comprising methanol, $DMM_1$ and formaldehyde) is continuously distilled from the tower top, and fed back to the reaction system and cooled through the pipeline 25, while the tower bottom liquid is delivered into the rectification tower C4 through the pipeline 26. The extraction agent distilled from the tower top is fed back to the extraction agent storage tank V1 through the pipeline 27 for reuse, while the tower bottom liquid is fed into the rectification tower C5 through the pipeline 28. The $DMM_2$ distilled from the tower top is fed back to the reaction unit through the pipeline 29 for reuse, while the product $DMM_{3-8}$ flowing out from the tower bottom is fed into the storage tank V8 through the pipeline 30.

(7) Dehydration of the Catalyst

The aqueous catalyst solution is continuously fed into the thin film evaporator S2 from the bottom of the extraction tower C2. Most of water is removed by rapid distillation at 60~70° C./−0.08~−0.09 MPa, while the catalyst and the aqueous formaldehyde solution are recycled to the catalyst storage tank V7 through the pipeline 31.

Specific preparation examples are provided below. With reference to the configuration in FIG. 1, the invention will be further explained by means of the Examples. For the direction of the materials during the whole process flow, FIG. 2 may be referred.

EXAMPLES

The catalysts used in the Examples below are represented as following:

Example 1

Figure 1:
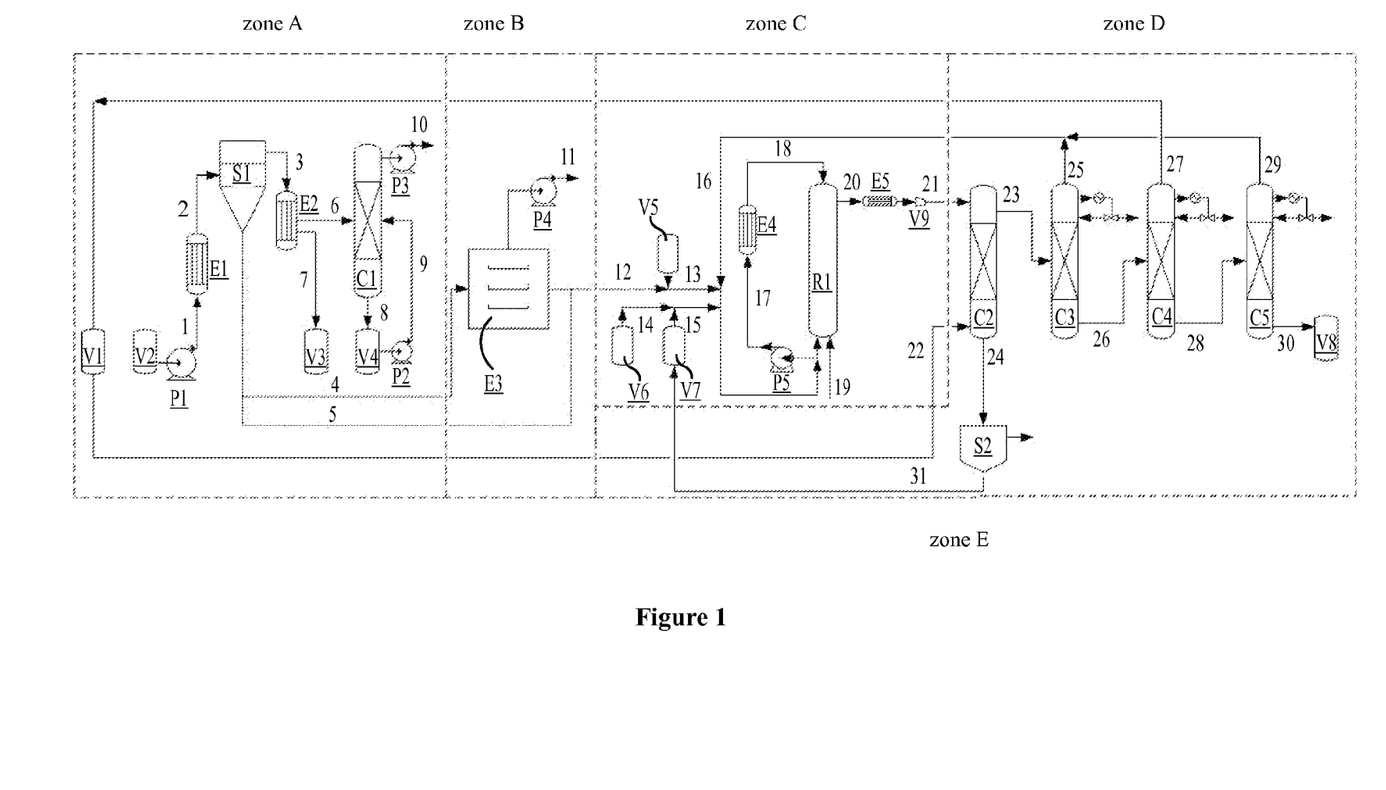
FIG. 1 is a schematic diagram of a reaction system for continuously preparing polymethoxy dimethyl ether of the invention.
Figure 2:
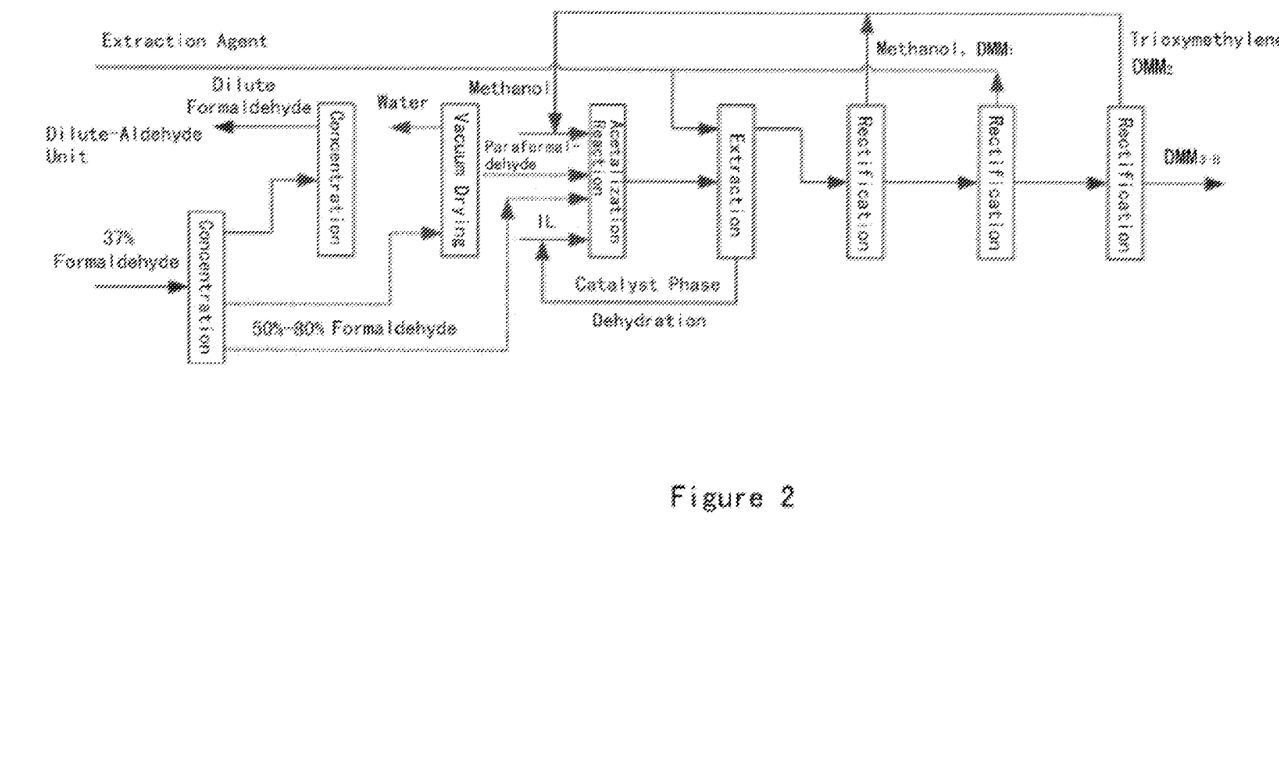
FIG. 2 is a diagram of the flowing direction of the reaction materials in the process of the invention.

In the process shown in FIG. 1, the reactor R1 was a shell and tube reactor. The reactor R1 and the reactor heat exchanger were communicated with each other circularly, the reaction liquid was circulated in the reactor and the heat exchanger, and the volume was 500 mL.

The air in the system was replaced by purging with high-purity nitrogen. To the formaldehyde concentrator S1, an aqueous formaldehyde solution having a concentration of 37 wt. % was continuously added at a feeding speed of 135 mL/h. The temperature of the concentrator S1 was controlled at 80~90° C., and the vacuum degree thereof was controlled at −0.05~−0.06 MPa. The vapor phase was fed into the dilute-aldehyde condenser E2 through the pipeline 3, and condensed to form liquid dilute formaldehyde, which was fed into the dilute-aldehyde receiving tank V3 through the pipeline 7 at a flow rate of 65 mL/h. The liquid phase was a formaldehyde solution of 60 wt. %, and delivered into the acetalization reactor R1 in C zone through the pipeline 5 at a flow rate of 70 mL/h.

To the reactor R1, the ionic liquid catalyst IL1 was added at a feeding speed of 9.8 g/h. When the catalyst solution began to circulate, the feeding was stopped, and the concentration of the catalyst was kept to be not less than 4 wt. %. The initial feeding speeds of the concentrated formaldehyde and methanol were 170 mL/h and 68 mL/h, respectively. When the reaction materials began to circulate, the feeding speed of the formaldehyde was 70 mL/h. The operation conditions of the reactor R1 were controlled as 125~130° C. and 3.5~4.0 MPa. The reactor effluent liquid was fed into the extraction tower C2. The feeding speed of the extraction agent, benzene, was 250 mL/h (being 1 fold more than the volume of the reaction liquid). The heavy phase (the catalyst and aqueous formaldehyde solution) was continuously fed into the film evaporator S2 from the tower bottom, where most of water was removed at 65° C./−0.085 MPa, after that the heavy phase was fed into the reactor for reuse. The light phase (the product phase) was continuously fed into the rectification tower C3 from the tower top. The light component, $DMM_1$, methanol and formaldehyde, was continuously distilled from the tower top at 40~65° C., and was fed back into the reaction unit for reuse, while the tower bottom liquid was fed into the rectification tower C4. The extraction agent, benzene, distilled from the tower top at 78~80° C. was fed back into the storage tank V1 for reuse, while the tower bottom liquid was fed into the rectification tower C5. $DMM_2$ and trioxymethylene (the by-product) distilled from the tower top at 98~110° C. were fed back to the reaction unit for reuse, while the product, $DMM_{3-8}$, flowing out from the tower bottom was fed into the product storage tank.

Quantitative analysis of the samples taken from the reaction liquid, the extract, the aqueous catalyst solution, the recycled material and the product at certain interval was carried out by using the gas chromatograph. The test was run for 100 h totally. The average values of the test result were listed in Table 1.

TABLE 1

| pipeline of sampling point | discharging speed mL/h | product distribution (%) | | | | | | | | | | | |
|---|---|---|---|---|---|---|---|---|---|---|---|---|---|
| | | benzene | methanol | form-aldehyde | trioxy-methylene | water | \multicolumn{8}{c}{$DMM_n$, n =} |
| | | | | | | | 1 | 2 | 3 | 4 | 5 | 6 | 7 | 8 |
| 5 | 70.0 | 0 | 0.1 | 60.0 | 0 | 39.9 | 0 | 0 | 0 | 0 | 0 | 0 | 0 | 0 |
| 21 | 245.0 | 0 | 8.9 | 15.0 | 0.6 | 28.4 | 21.1 | 12.5 | 5.2 | 2.6 | 1.5 | 0.2 | 0.01 | 0 |
| 23 | 380.5 | 60.5 | 6.2 | 0.5 | 0.5 | 0.4 | 15.6 | 9.2 | 3.8 | 2.0 | 1.1 | 0.2 | 0.01 | 0 |
| 24 | 115.5 | 1.3 | 1.1 | 31.0 | 0 | 56.6 | 1.2 | 0.2 | 0 | 0 | 0 | 0 | 0 | 0 |
| 25 | 73.5 | 0.4 | 27.8 | 1.4 | 0 | 0.1 | 70.0 | 0.2 | 0 | 0 | 0 | 0 | 0 | 0 |
| 29 | 32.0 | 0.3 | 0 | 0 | 4.5 | 0.5 | 0 | 94.5 | 0.2 | 0 | 0 | 0 | 0 | 0 |
| 30 | 23.5 | 0 | 0 | 0 | 0 | 0 | 0 | 1.1 | 54.1 | 27.0 | 15.6 | 2.1 | 0.1 | 0 |
| 31 | 70.0 | 0 | 0.1 | 55.7 | 0 | 30.5 | 0 | 0 | 0 | 0 | 0 | 0 | 0 | 0 |

The reaction effluent liquid (21) comprised 4% of the catalyst.
The aqueous catalyst solution (24) comprised 8.6% of the catalyst after extraction.
The catalyst phase (31) comprised 13.7% of the catalyst after dehydration.

Example 2

The basic procedure and the equipments were same as in Example 1, except that the catalyst was the ionic liquid IL2 and the concentration of the formaldehyde solution is 80 wt. %. After running for 100 h continuously, $DMM_{3-8}$ product was obtained at 24.0 mL/h (from the pipeline 30).

Example 3

The basic procedure and the equipments as well as the parameters thereof were same as in Example 1, except that toluene was used as the extraction agent at a flow rate of 490 mL/h. After running for 100 h continuously, $DMM_{3-8}$ product was obtained at 23.0 mL/h (from the pipeline 33).

Example 4

In the process shown in FIG. 1, the reactor R1 was a shell and tube reactor. The reactor R1 and the reboiler were communicated with each other circularly. The reaction liquid was circulated in the reactor and the heat exchanger, and the volume was 500 mL.

The air in the system was replaced by purging with high-purity nitrogen. To the formaldehyde concentrator S1, an aqueous formaldehyde solution having a concentration of 37 wt. % was continuously added at a feeding speed of 105 mL/h. The temperature of the concentrator S1 was controlled at 80~90° C., and the vacuum degree thereof was controlled at −0.05~−0.06 MPa. The vapor phase was fed into the dilute-aldehyde condenser E2 through the pipeline 3, and condensed to form liquid dilute formaldehyde, which was fed into the dilute-aldehyde receiving tank V3 through the pipeline 7 at a flow rate of 63 mL/h. The liquid phase was a formaldehyde solution of 80 wt. %, delivered into vacuum drier E3 in zone B through the pipeline 4 at a flow rate of 42 mL/h, and vacuum-dried under the conditions of 60~80° C. and −0.1~−0.05 MPa, so as to obtain paraformaldehyde having a polymerization degree of 8~16. The paraformaldehyde may be fed into the acetalization reactor R1 through the pipeline 12 (at 34 g/h).

To the reactor R1, the ionic liquid catalyst IL1 was added at a feeding speed of 9.8 g/h. When the catalyst solution began to circulate, the feeding was stopped, and the concentration of the catalyst was kept to be not less than 4 wt. %. The initial feeding speeds of paraformaldehyde and methanol were 72 g/h and 47.5 mL/h, respectively. When the reaction materials began to circulate, the feeding speeds of the formaldehyde and methanol were 34 g/h and 36 mL/h, respectively. The operation conditions of the reactor R1 were controlled as 125~130° C. and 3.5~4.0 MPa. The reactor effluent liquid was fed into the extraction tower C2. The feeding speed of the extraction agent, benzene, was 245 mL/h (being 1 fold more than the volume of the reaction liquid). The heavy phase (the catalyst, aqueous formaldehyde solution) was continuously fed into the film evaporator S2 from the tower bottom, where most of water was removed at 65° C./−0.085 MPa, was after that the heavy phase was fed into the reactor for reuse. The light phase (the product phase) was continuously fed into the rectification tower C3 from the tower top. The light components, $DMM_1$, formaldehyde and methanol were continuously distilled from the tower top at 40~65° C., and fed back into the reaction unit for reuse, while the tower bottom liquid was fed into the rectification tower C4. The extraction agent, benzene, distilled from the tower top at 78~80° C. was fed back into the storage tank V1 for reuse, while the tower bottom liquid was fed into the rectification tower C5. $DMM_2$ and trioxymethylene (the by-product) distilled from the tower top at 98~110° C. were fed back to the reaction unit for reuse, while the product $DMM_{3-8}$ flowing out from the tower bottom was fed into the product storage tank.

Quantitative analysis of the samples taken from the reaction liquid, the extract, the aqueous catalyst solution, the recycled material and the product at certain interval was carried out by using the gas chromatograph. The test was run for 100 h totally. The average values of the test result were listed in Table 2.

Example 5

The basic procedure and the equipments were same as in Example 4, except that the catalyst was IL4 and the used amount thereof is 6 wt. % of the total feeding materials. After running for 100 h continuously, $DMM_{3-8}$ product was obtained at 53.5 mL/h (from the pipeline 30).

Example 6

The basic procedure and the equipments were same as in Example 4, except that the catalyst was IL5 and the used amount thereof is 2 wt. % of the total feeding materials. After running for 100 h continuously, $DMM_{3-8}$ product was obtained at 42.5 mL/h (from the pipeline 30).

Example 7

The basic procedure and the equipments were same as in Example 4, except that the molar ratio between formaldehyde and methanol was 1:1. After running for 100 h continuously, $DMM_{3-8}$ product was obtained at 40.5 mL/h (from the pipeline 30).

The above-mentioned Examples merely describe the preferred embodiments of the invention, and do not limit the scope of the invention. Various modifications and changes can be made by those skilled in the art on the technical solutions of the invention without departing from the spirit of the invention, all of which fall into the protection scope of the invention defined by the claims.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

The invention claimed is:

1. A reaction system for continuously preparing polymethoxy dimethyl ether with an aqueous formaldehyde solution or paraformaldehyde as raw material, which comprises:
   1) a formaldehyde-concentrating unit, which is used to concentrate an aqueous formaldehyde solution of 37 to 40 wt. % to obtain a concentrated formaldehyde of 50 to 80 wt. %;
   2) a vacuum-drying unit, which is used to polymerize the concentrated formaldehyde obtained from the formaldehyde-concentrating unit to paraformaldehyde;
   3) an acetalization reaction unit, which is used to subject the concentrated formaldehyde obtained from the formaldehyde-concentrating unit, the paraformaldehyde obtained from the vacuum-drying unit or paraformaldehyde added directly from the exterior to an acetalization reaction with methanol in the presence of an acidic ionic liquid catalyst, so as to obtain a crude product $DMM_{1-8}$; and

TABLE 2

| pipeline of sampling point | discharging speed mL/h | product distribution (%) | | | | | | | | | | | | |
|---|---|---|---|---|---|---|---|---|---|---|---|---|---|---|
| | | benzene | methanol | form- aldehyde | trioxy- methylene | water | $DMM_n$, n = | | | | | | | |
| | | | | | | | 1 | 2 | 3 | 4 | 5 | 6 | 7 | 8 |
| 4 | 42.0 | 0 | 0.01 | 80.0 | 0 | 20 | 0 | 0 | 0 | 0 | 0 | 0 | 0 | 0 |
| 12 | 34.0 | 0 | 0 | 98.0 | 0 | 2 | 0 | 0 | 0 | 0 | 0 | 0 | 0 | 0 |
| 21 | 245.0 | 0 | 3.8 | 27.7 | 1.6 | 15.7 | 15.6 | 14.2 | 10.8 | 6.4 | 2.8 | 1.0 | 0.3 | 0.1 |
| 23 | 383.0 | 58.7 | 2.7 | 0.5 | 1.1 | 0.1 | 11.4 | 10.4 | 7.9 | 4.7 | 2.0 | 0.7 | 0.2 | 0 |
| 24 | 107.0 | 0.5 | 0.3 | 46.2 | 0 | 33.6 | 0.8 | 0.1 | 0 | 0 | 0 | 0 | 0 | 0 |
| 25 | 47.5 | 0.4 | 17.7 | 1.5 | 0 | 0.1 | 80.4 | 0.1 | 0 | 0 | 0 | 0 | 0 | 0 |
| 29 | 38.0 | 0.3 | 0 | 0 | 10.0 | 0.5 | 0 | 89.0 | 0.2 | 0 | 0 | 0 | 0 | 0 |
| 30 | 52.5 | 0.2 | 0 | 0 | 0 | 0 | 0 | 1.1 | 49.5 | 29.6 | 13.0 | 4.6 | 1.4 | 0.03 |

The aqueous catalyst solution (24) comprised 18.5% of the catalyst after extraction.

4) a product-separating unit, which is used to separate the desired product polymethoxy dimethyl ether $DMM_{3-8}$ from the crude product obtained from the acetalization reaction unit.

2. The reaction system according to claim 1, characterized in that the formaldehyde-concentrating unit comprises a formaldehyde heater, a formaldehyde concentrator, a dilute-aldehyde condenser, a column washer and a washing liquor tank, wherein the aqueous formaldehyde solution is evaporated in the formaldehyde heater to give a vapor-liquid mixed fluid; the vapor-liquid mixed fluid is fed into the formaldehyde concentrator to give a liquid concentrated formaldehyde having a concentration of 50 to 80 wt. %, and the gas generated during this process is fed into the dilute-aldehyde condenser to recover formaldehyde, the non-condensable gas out from the dilute-aldehyde condenser is fed into the column washer to be absorbed by the washing liquor and entered into the washing liquor tank.

3. The reaction system according to claim 1, characterized in that the vacuum-drying unit is a continuous vacuum dryer, and under the conditions of 60 to 80° C. and a gauge pressure of −0.1 to −0.05 MPa, the concentrated formaldehyde obtained from the formaldehyde-concentrating unit is polymerized into a paraformaldehyde having a polymerization degree of 8 to 16.

4. The reaction system according to claim 1, characterized in that the acetalization unit comprises a single-stage or multi-stage reactor and a vapor condenser.

5. The reaction system according to claim 4, characterized in that the single-stage or multi-stage reactor is a single-stage or multi-stage shell and tube reactor or an overflow kettle.

6. The reaction system according to claim 1, characterized in that the reaction system further comprises a catalyst-regenerating unit, which comprises a thin film evaporator and is used to receive the heavy phase separated from the product-separating unit and to recycle the catalyst in the heavy phase back to the acetalization reaction unit after the catalyst is dehydrated.

7. The reaction system according to claim 6, characterized in that the product-separating unit comprises an extraction tower and a single-stage or multi-stage rectification tower, the extraction tower and the single-stage or multi-stage rectification tower are connected with each other in series; and the extraction tower separates the crude product into a light phase and a heavy phase, wherein the heavy phase comprises the acidic ionic liquid catalyst, formaldehyde and water, and the light phase comprises unreacted methanol and formaldehyde, $DMM_{1-8}$ as well as an extraction agent; the light phase is continuously flowed into a rectification unit from the top of the extraction tower, so that the recycled material comprising formaldehyde, methanol and $DMM_{1-2}$, the extraction agent and the desired product $DMM_{3-8}$ are separated; the recycled material is fed back to the acetalization reaction unit; the extraction agent is fed back to the extraction tower for reuse; the heavy phase is flowed into the catalyst-regenerating unit from the tower bottom.

8. The reaction system according to claim 7, characterized in that the rectification tower comprises a light component rectification tower, an extraction agent rectification tower and a product rectification tower.

9. The reaction system according to claim 7, characterized in that the rectification tower is a tray tower or a packed tower, and the number of tower tray is 3 to 10.

10. The reaction system according to claim 2, characterized in that the acetalization unit comprises a single-stage or multi-stage reactor and a vapor condenser.

11. The reaction system according to claim 3, characterized in that the acetalization unit comprises a single-stage or multi-stage reactor and a vapor condenser.

12. The reaction system according to claim 2, characterized in that the reaction system further comprises a catalyst-regenerating unit, which comprises a thin film evaporator and is used to receive the heavy phase separated from the product-separating unit and to recycle the catalyst in the heavy phase back to the acetalization reaction unit after the catalyst is dehydrated.

13. The reaction system according to claim 3, characterized in that the reaction system further comprises a catalyst-regenerating unit, which comprises a thin film evaporator and is used to receive the heavy phase separated from the product-separating unit and to recycle the catalyst in the heavy phase back to the acetalization reaction unit after the catalyst is dehydrated.

* * * * *